United States Patent
Meissner et al.

(10) Patent No.: US 10,398,101 B2
(45) Date of Patent: Sep. 3, 2019

(54) TOMATO ROOTSTOCK VARIETY 'RTS-188'

(71) Applicant: Rootility Ltd., Ashkelon (IL)

(72) Inventors: Rafael Meissner, Rehovot (IL); Ari Efrati, Shafir (IL); Omri Lifshitz, Kfar Bilu (IL); Shachaf Ein-Gedy, Kfar Uriya (IL); Naama Aviv, Netic Haasara (IL)

(73) Assignee: Rootility Ltd., Ashkelon (IL)

(*) Notice: Subject to any disclaimer, the term of this patent is extended or adjusted under 35 U.S.C. 154(b) by 5 days.

(21) Appl. No.: 15/682,405

(22) Filed: Aug. 21, 2017

(65) Prior Publication Data

US 2018/0049386 A1   Feb. 22, 2018

Related U.S. Application Data

(60) Provisional application No. 62/378,072, filed on Aug. 22, 2016.

(51) Int. Cl.
*A01H 5/10* (2018.01)
*A01H 5/08* (2018.01)

(52) U.S. Cl.
CPC ..................... *A01H 5/08* (2013.01)

(58) Field of Classification Search
None
See application file for complete search history.

(56) References Cited

U.S. PATENT DOCUMENTS

| 8,106,273 B2 | 1/2012 | Kim et al. |
| 8,466,350 B2 * | 6/2013 | Fowler ..................... A01H 5/08 800/317.4 |
| 9,642,319 B2 | 5/2017 | Meissner et al. |
| 2016/0157449 A1 | 6/2016 | Meissner et al. |

* cited by examiner

*Primary Examiner* — Jason Deveau Rosen
(74) *Attorney, Agent, or Firm* — Morrison & Foerster LLP

(57) ABSTRACT

Tomato rootstock variety designated 'RTS-188' is disclosed. The invention relates to the seeds of tomato rootstock 'RTS-188', to the plants of tomato rootstock 'RTS-188', and to methods for producing plants, and to methods for producing other tomato rootstock lines, cultivars, transgenic plants or hybrids derived from the tomato rootstock variety 'RTS-188'.

13 Claims, 7 Drawing Sheets
(7 of 7 Drawing Sheet(s) Filed in Color)

TOMATO ROOTSTOCK VARIETY 'RTS-188'

CROSS REFERENCE TO RELATED APPLICATIONS

This application claims the benefit of U.S. Provisional Application No. 62/378,072, filed Aug. 22, 2016, which is hereby incorporated by reference in its entirety.

FIELD

This invention relates to the field of plant breeding. In particular, this invention relates to new and distinctive tomato, *Solanum lycopersicon*, rootstock variety designated 'RTS-188'.

BACKGROUND

Cultivated and commercial forms of tomato generally belong to a species most frequently referred to as *Lycopersicon esculentum* Miller (also known as *Solanum lycopersicum*) that is grown for its fruit and which is widely used as a fresh market or processed product. As a crop, tomato is grown commercially wherever environmental conditions permit the production of an economically viable yield. The size of tomato fruits may range from small to large and there are cherry, plum, pear, standard, and beefsteak types. Tomatoes may be grouped by the amount of time it takes for the plants to mature fruit for harvest; in general the cultivars are considered to be early, midseason or late-maturing. Tomatoes can also be grouped by the plant's growth habit, which can be determinate or indeterminate. Determinate plants tend to grow their foliage first, then set flowers that mature into fruit if pollination is successful. All of the fruit tend to ripen on a plant at about the same time. Indeterminate tomatoes start out by growing some foliage, then continue to produce foliage and flowers throughout the growing season. These plants will tend to have tomato fruit in different stages of maturity at any given time. More recent developments in tomato breeding have led to a wider array of fruit color. In addition to the standard red ripe color, tomatoes can be creamy white, lime green, pink, yellow, golden, or orange.

The first largest processing market and second largest fresh market for tomatoes in the United States is in California, where processing tomatoes are harvested by machine. The majority of fresh market tomatoes are harvested by hand at vine ripe and mature green stages of ripeness. Fresh market tomatoes are available in the United States year round. Process tomato season in California is from late June to October. Process tomatoes are used in many forms, as canned tomatoes, tomato juice, tomato sauce, puree, paste and catsup. Of the 500,000 acres of tomatoes that are grown annually in the US, approximately 40% are grown for fresh market consumption, while the remaining are grown for processing.

*Lycopersicon* is a relatively small genus within the extremely large and diverse family Solanaceae, which is considered to consist of around 90 genera including pepper, tobacco, and eggplant. The genus *Lycopersicon* has been divided into two subgenera, the *esculentum* complex which contains those species that can easily be crossed with the commercial tomato and the *peruvianum* complex which contains those species which are crossed with considerable difficulty (Stevens, M., and Rick, C. M. 1986. Genetics and Breeding. In: The Tomato Crop. A scientific basis for improvement, pp. 35-109. Atherton, J., Rudich, G. (eds.). Chapman and Hall, New York). Due to its value as a crop, *L. esculentum* Miller has become widely disseminated all over the world. Even if the precise origin of the cultivated tomato is still somewhat unclear, it seems to come from the Americas, being native to Ecuador, Peru and the Galapagos Islands and initially cultivated by Aztecs and Incas as early as 700 AD. Mexico appears to have been the site of domestication and the source of the earliest introduction. It is thought that the cherry tomato, *L. esculentum* var. *cerasiforme*, is the direct ancestor of modern cultivated forms.

Tomato grafting has been utilized in Asia and Europe for greenhouse and high tunnel production and is gaining popularity in the United States. One advantage of grafting is that rootstocks may be used that provide or increase resistance against, for example, fungal and viral diseases. In addition to providing or increasing resistance against such diseases, the use of grafting may also increase tolerance against different abiotic stresses, such as drought tolerance, salinity tolerance, flooding/water tolerance and heat and cold temperature tolerance. There are several methods for grafting tomatoes. The most common grafting methods include tongue approach/approach graft, hole insertion/terminal/top insertion graft, one cotyledon/slant/splice/tube graft, and cleft/side insertion graft.

Tomato is a simple diploid species with twelve pairs of differentiated chromosomes. The cultivated tomato is self-fertile and almost exclusively self-pollinating. The tomato flowers are hermaphrodites. Commercial cultivars were initially open-pollinated, but most have now been replaced by better yielding hybrids. Due to its wide dissemination and high value, tomato has been intensively bred.

It is becoming more and more challenging for farmers globally to satisfy the increasing worldwide demand for food. Progressively adverse environmental conditions steadily decrease available arable land. Furthermore, a growing global population presents serious challenges to the agricultural industry. Thus, there is a need to overcome the current constraints (e.g., land, water, etc.) and reduce the risks of climate volatility. Improving crop production is essential to the future of sustainable agriculture.

Current agricultural systems use traditional breeding methods or transgenic technologies to develop improved plant varieties. Presently lacking is a breeding method which places emphasis on the plant organ (the root) responsible for supplying vital nutrients to the plant, thus directly impacting the plant's ultimate performance, yield, and its ability to tolerate abiotic stress.

Tomato is an important and valuable vegetable crop. Thus, there is a continued need for new tomato varieties. In particular, there is a need for an improved non-GMO tomato rootstock variety that is stable, high yielding, and agronomically sound. A rootstock variety that is tolerant to abiotic stress conditions (for example, cold, heat, salinity and/or drought) and can overcome sub-optimal growing conditions that limit crop yield, for example for growing processing tomatoes, is also needed.

SUMMARY

In order to meet this need, the present invention provides improved tomato rootstock variety designated 'RTS-188'. Tomato rootstock variety 'RTS-188' is graft compatible with tomato scion cultivars and other vegetable crop scions including pepper, eggplant and potato, and confers resistance and/or tolerance to cold stress, heat stress, and drought, and confers increased yield on grafted plants. The tomato rootstock variety 'RTS-188' disclosed herein is unique in that it is useful for grafting greenhouse tomatoes and processing tomatoes. For greenhouse tomatoes a ton/ dunam yield increase of up to 20% has been obtained with 'RTS-188'. For processing tomatoes a ton/acre yield increase of up to 100% has been obtained with 'RTS-188'.

Tomato rootstock variety 'RTS-188' disclosed herein is also unique in that it is especially suitable for automated grafting by an automated grafting machine due to having a strong and long hypocotyl.

Tomato rootstock variety 'RTS-188' also confers resistance and/or tolerance to Fusarium wilt race 3 on the grafted tomato plants and may also confer resistance and/or tolerance to one or more of Fusarium wilt race 1, Fusarium wilt race 2, Verticillium wilt race 1 and Tobacco mosaic virus (TMV).

The tomato rootstock variety designated 'RTS-188' may be grafted with a scion utilizing any suitable grafting methodology known in the art. Examples of suitable grafting methodologies include, without limitation, cleft grafting, approach grafting, micrografting, tube grafting, side insertion grafting, and top insertion grafting. Cleft grafting involves cutting a V-shape into the rootstock and inserting a complementing wedge-shaped scion. The graft may be then held with a small clip until healing occurs. Approach grafting, also known as tongue approach grafting (TAG), involves notching opposing sides of the stems of the rootstock and scion, and then using a clip to hold the stems together while they fuse. Once the graft has healed, the scion of the desired rootstock plant may be removed above the graft site, and the unused rootstock from scion plant may be detached from the scion below the graft site. Micrografting, also known as splice grafting, is a technique that has been recently integrated into micropropagation production for hybrid tomato. Micrografting involves utilizing micropropagated scion shoots that may be grafted onto approximately three week-old rootstock seedlings. In some embodiments, micrografting is utilized for commercial scale tomato grafting. Tube grafting involves severing the scion and rootstock as seedlings and attaching the severed rootstock seedling to the severed scion seedling with a small, silicone tube with or without a clip. Tube grafting can be highly effective, as it may be carried out when plants are very small, thereby eliminating the need for large healing chambers while increasing the output. Although less frequently used on a commercial scale, side insertion grafting and top insertion grafting are also contemplated herein.

In one embodiment, the present invention is directed to seed of a tomato rootstock designated as 'RTS-188' having ATCC Accession Number PTA-124244. In one embodiment, the present invention is directed to a tomato plant and parts isolated therefrom produced by growing 'RTS-188' tomato rootstock seed. In another embodiment, the present invention is directed to a tomato plant and parts isolated therefrom, or a transgenic tomato plant and parts isolated therefrom, having all the physiological and morphological characteristics of a tomato plant produced by growing 'RTS-188' tomato rootstock seed having ATCC Accession Number PTA-124244. In still another embodiment, the present invention is directed to an F1 hybrid tomato seed, plants grown from the seed, and rootstocks, leaves, ovules, pollen, fruit, cotyledons, embryos, meristems, anthers, roots, root tips, pistils, flowers, stems, calli, stalks, hypocotyl, and pericarps isolated therefrom having tomato rootstock variety 'RTS-188' as a parent, wherein 'RTS-188' is grown from 'RTS-188' tomato rootstock seed having ATCC Accession Number PTA-124244. In some embodiments, the F1 hybrid is a transgenic plant. In another embodiment, the present invention is directed to a tomato plant and parts isolated therefrom having all the physiological and morphological characteristics of a tomato plant produced by growing 'RTS-188' tomato rootstock seed having ATCC Accession Number PTA-124244. In some embodiments, the tomato plant is a transgenic plant. In still another embodiment, the present invention is directed to an F1 hybrid tomato seed, plants grown from the seed, and rootstocks, leaves, ovules, pollen, fruit, cotyledons, embryos, meristems, anthers, roots, root tips, pistils, flowers, stems, calli, stalks, hypocotyl, and pericarps isolated therefrom having 'RTS-188' as a parent, wherein 'RTS-188' is grown from 'RTS-188' tomato rootstock seed having ATCC Accession Number PTA-124244. In some embodiments, the plant grown from the F1 hybrid seed is a transgenic plant.

Tomato plant parts include rootstocks, leaves, ovules, pollen, fruit, cotyledons, embryos, meristems, anthers, roots, root tips, pistils, flowers, stems, calli, stalks, hypocotyl, pericarps, and the like. In another embodiment, the present invention is further directed to tomato fruit, rootstocks, stems, leaves, parts of leaves, roots, root tips, pollen, ovules, and flowers isolated from plants of tomato rootstock 'RTS-188' In another embodiment, the present invention is further directed to rootstocks derived from 'RTS-188' tomato plants. In another embodiment, the present invention is further directed to tissue culture or cells derived from plants of tomato rootstock 'RTS-188'.

In yet another embodiment, the present invention is further directed to a method of selecting tomato plants by a) growing 'RTS-188' tomato rootstock plants wherein the 'RTS-188' plants are grown from tomato seed having ATCC Accession Number PTA-124244; and b) selecting a plant from step a). In another embodiment, the present invention is further directed to tomato plants, plant parts and seeds produced by the tomato plants, where the tomato plants are isolated by the selection method of the invention. In another embodiment, the present invention is further directed to a method of breeding tomato plants by crossing a tomato plant with a plant grown from 'RTS-188' tomato rootstock seed having ATCC Accession Number PTA-124244. In some embodiments, at least one of the plants of the crossing is a transgenic plant. In still another embodiment, the present invention is further directed to tomato plants, tomato parts from the tomato plants, and seeds produced therefrom where the tomato plant is isolated by the breeding method of the invention.

In yet another embodiment, provided herein is a tomato plant comprising a rootstock and a scion engrafted onto the rootstock, wherein said rootstock is from tomato rootstock variety designated 'RTS-188'. In yet another embodiment, provided herein is a method of producing a tomato plant comprising a) providing a 'RTS-188' rootstock; and b) grafting onto the 'RTS-188' rootstock a scion, thereby generating a tomato plant. In preferred embodiments, the scion is a heterologous Solanum lycopersicon scion for growing greenhouse or open field, fresh market or processing tomatoes.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2A shows the abaxial view of the leaves. FIG. 2B shows the adaxial view of the leaves. In the photographs, each square on the sheet is 1 cm$^2$.

FIG. 6A shows 'N6415' tomato plants grafted on tomato rootstock variety 'RTS-188'. FIG. 6B shows non-grafted 'N6415' tomato plants. The dotted line represents a demarcation between the grafted and non-grafted tomato plants. All plants were planted in parallel in a field in California, United States.

DETAILED DESCRIPTION

Definitions

Figure 1:
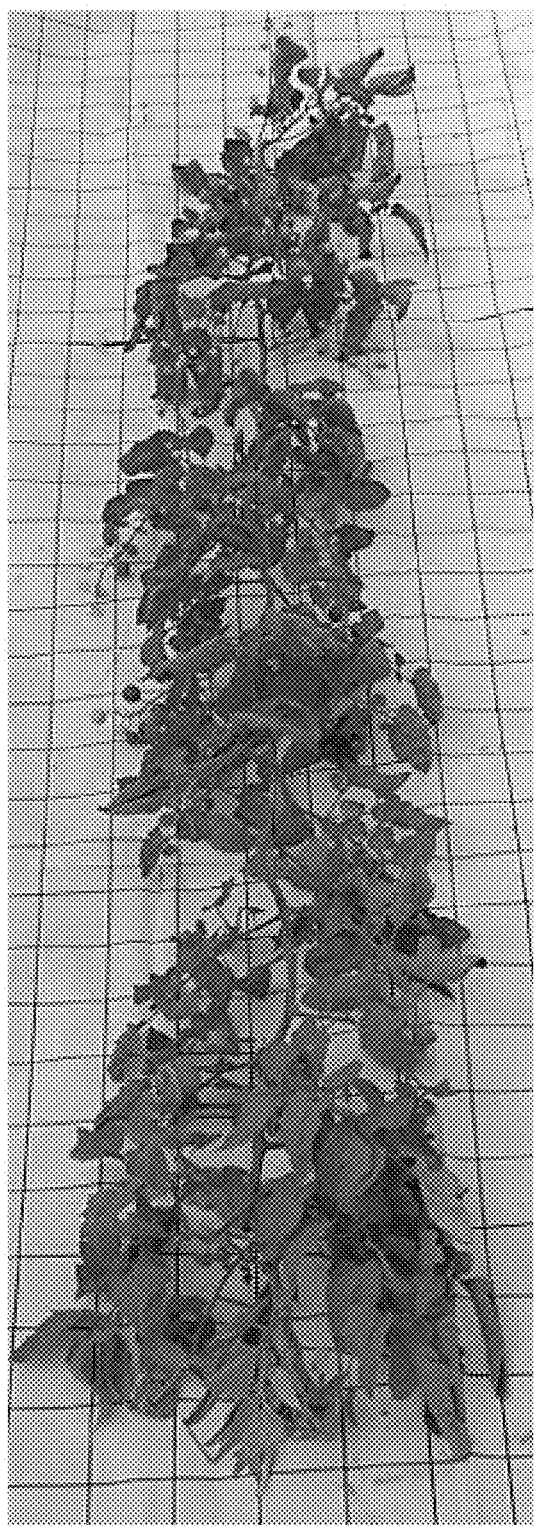
FIG. 1 illustrates a 100-day old plant from the tomato rootstock variety 'RTS-188'. In the photograph, each square on the sheet is 10 $cm^2$.

In the description and tables that follow, a number of terms are used. In order to provide a clear and consistent understanding of the specification and claims, the following definitions are provided.

Allele: The allele is any of one or more alternative form of a gene, all of which alleles relates to one trait or characteristic. In a diploid cell or organism, the two alleles of a given gene occupy corresponding loci on a pair of homologous chromosomes.

Attachment point: The point on the tomato fruit where the fruit is connected to the tomato plant.

Backcrossing: Backcrossing is a process in which a breeder repeatedly crosses hybrid progeny back to one of the parents, for example, a first generation hybrid $F_1$ with one of the parental genotypes of the $F_1$ hybrid.

BRIX: Means a percentage by weight of the fruit of sugar in solution measured using a refractometer, wherein the fruit is cut in half and the juice within the fruit is squeezed onto a lens. The juice on the lens is then measured by the refractometer.

Determinate tomato: A variety that comes to fruit all at once, then stops bearing. Determinate varieties are best suited for commercial growing since they can be harvested all at once.

Essentially all the physiological and morphological characteristics: A plant having essentially all the physiological and morphological characteristics of another plant means a plant having the physiological and morphological characteristics, except for the characteristics derived from the converted gene, of the other plant.

Flesh color: The color of the tomato flesh that can range from orange-red to dark red when at ripe stage (harvest maturity).

Fruit: A ripened ovary, together with any other structures that ripen with the ovary and form a unit.

Grafting: Grafting refers to attaching tissue from one plant to another plant so that the vascular tissues of the two tissues join together.

pH: The pH is a measure of, e.g., fruit acidity. A pH under 4.35 is desirable to prevent bacterial spoilage of finished products. pH rises as fruit matures.

Plant part: A plant part means any part of a plant including, for example, a cell, protoplast, embryo, pollen, ovule, flower, leaf, stem, cotyledon, hypocotyl, meristematic cell, root, root tip, pistil, anther, shoot tip, shoot, fruit and petiole.

Predicted paste bostwick: The predicted paste bostwick is the flow distance of tomato paste diluted to 12 degrees brix and heated prior to evaluation. Dilution to 12 degrees brix for bostwick measurement is a standard method used by industry to evaluate product consistency. The lower the number, the thicker the product and therefore more desirable in consistency oriented products such as catsup. The following formula is usually used to evaluate the predicted paste bostwick: Predicted paste bostwick=−11.53+ (1.64*juice brix)+(0.5*juice bostwick).

Regeneration: Regeneration refers to the development of a plant from tissue culture.

Relative maturity: Relative maturity is an indication of time until a tomato genotype is ready for harvest. A genotype is ready for harvest when 90% or more of the tomatoes are ripe.

Resistance and Tolerance: These terms are used interchangeably herein and describe plants that show no symptoms or significantly reduced symptoms to a specified biotic pathogen, abiotic stress, or environmental stress.

Rootstock: A root and its associated growth buds, used as a stock in plant propagation. As disclosed herein, such roots may be selected from a plant, for example for the resistance of its roots to diseases or stress (e.g., heat, cold, salinity etc.).

Scion: A part of a plant that is attached to a rootstock. A scion plant may be selected for its stems, leaves, flowers, or fruits. A selected scion may be used with the disclosed variety for greenhouse or open field, fresh market or processing tomatoes.

Semi-erect habit: A semi-erect plant has a combination of lateral and upright branching and has an intermediate-type habit between a prostate plant habit, having laterally growing branching with fruits most of the time on the ground and an erect plant habit has branching going straight up with fruit being off the ground.

Single gene converted: Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids: Soluble solids refer to the percent of solid material found in the fruit tissue, the vast majority of which is sugars. Soluble solids are directly related to finished processed product yield of pastes and sauces. Soluble solids are estimated with a refractometer, and measured as degrees brix.

Quantitative Trait Loci (QTL): Quantitative trait loci refer to genetic loci that control to some degree numerically representable traits that are usually continuously distributed.

Uniform ripening: Refers to a tomato that ripens uniformly, i.e., one that has no green discoloration on the shoulders. The uniform ripening is controlled by a single recessive gene.

Vegetative propagation: Means taking part of a plant and allowing that plant part to form roots where plant part is defined as leaf, pollen, embryo, cotyledon, hypocotyl, meristematic cell, root, root tip, pistil, anther, flower, shoot tip, shoot, stem, fruit and petiole.

Viscosity: The viscosity or consistency of tomato products is affected by the degree of concentration of the tomato, the amount of and extent of degradation of pectin, the size, shape and quality of the pulp, and probably to a lesser extent, by the proteins, sugars and other soluble constituents. The viscosity is measured in Bostwick centimeters by using instruments such as a Bostwick Consistometer.

Overview of Tomato Rootstock Variety 'RTS-188'

Described herein is a new and distinct tomato rootstock variety named 'RTS-188', which has superior characteristics. In one embodiment, tomato plants of tomato rootstock variety 'RTS-188' exhibit tolerance and/or resistance to cold stress (e.g., exhibit continuous development in chilling temperatures and/or frost), confer tolerance and/or resistance to cold stress to grafted plants, and confer increased scion yields when grafted.

In another embodiment, tomato plants of tomato rootstock variety 'RTS-188' exhibit tolerance and/or resistance to heat stress (e.g., exhibit continuous development in hot temperatures), confer tolerance and/or resistance to heat stress to grafted plants, and confer increased scion yields when grafted.

In another embodiment, tomato plants of tomato rootstock variety 'RTS-188' exhibit tolerance and/or resistance to drought stress (e.g., exhibit continuous development under drought), confer tolerance and/or resistance to drought stress to grafted plants, and confer increased scion yields when grafted.

In another embodiment, tomato plants of tomato rootstock variety 'RTS-188' are especially suitable for automated grafting by an automated grafting machine.

Figures 6A, 6B:
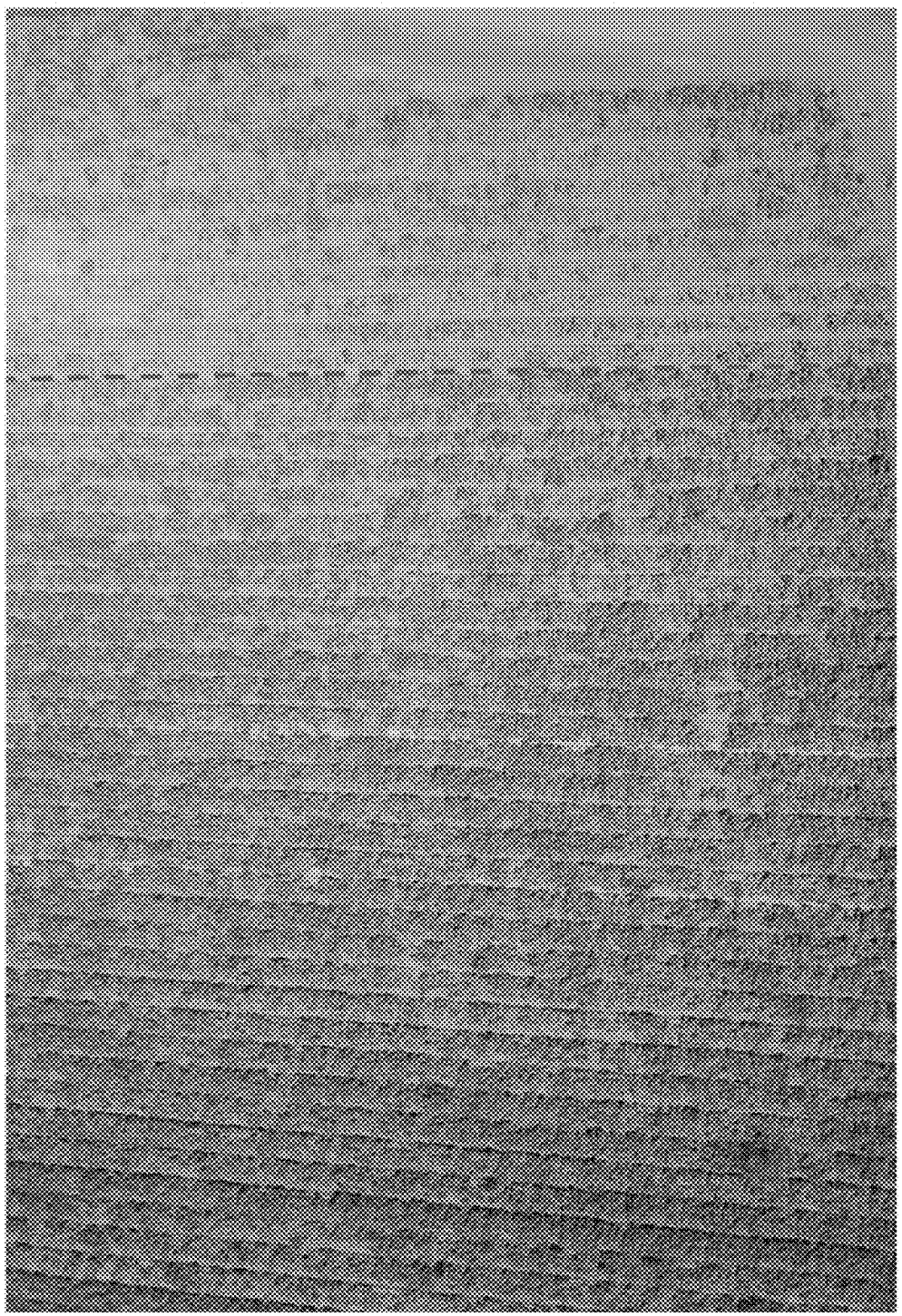
FIG. 6A and FIG. 6B depict a field infected with Fusarium wilt race 3 showing the difference in growth between grafted tomato plants ('N6415' tomato plants grafted on tomato rootstock variety 'RTS-188') and non-grafted ('N6415') tomato plants.

In another embodiment, tomato rootstock variety 'RTS-188' confers resistance and/or tolerance to Fusarium wilt race 3 to grafted plants (FIGS. 6A and 6B).

In another embodiment tomato rootstock variety 'RTS-188' confers resistance and/or tolerance to one or more of Fusarium wilt race 1, Fusarium wilt race 2, Verticillium wilt race 1 and Tobacco mosaic virus (TMV) to grafted plants.

The tomato rootstock variety 'RTS-188' is uniform and stable within commercially acceptable limits. As is true with other tomato plant varieties, a small percentage of variants can occur within commercially acceptable limits for almost any characteristic during the course of repeated multiplication.

Figure 2A:
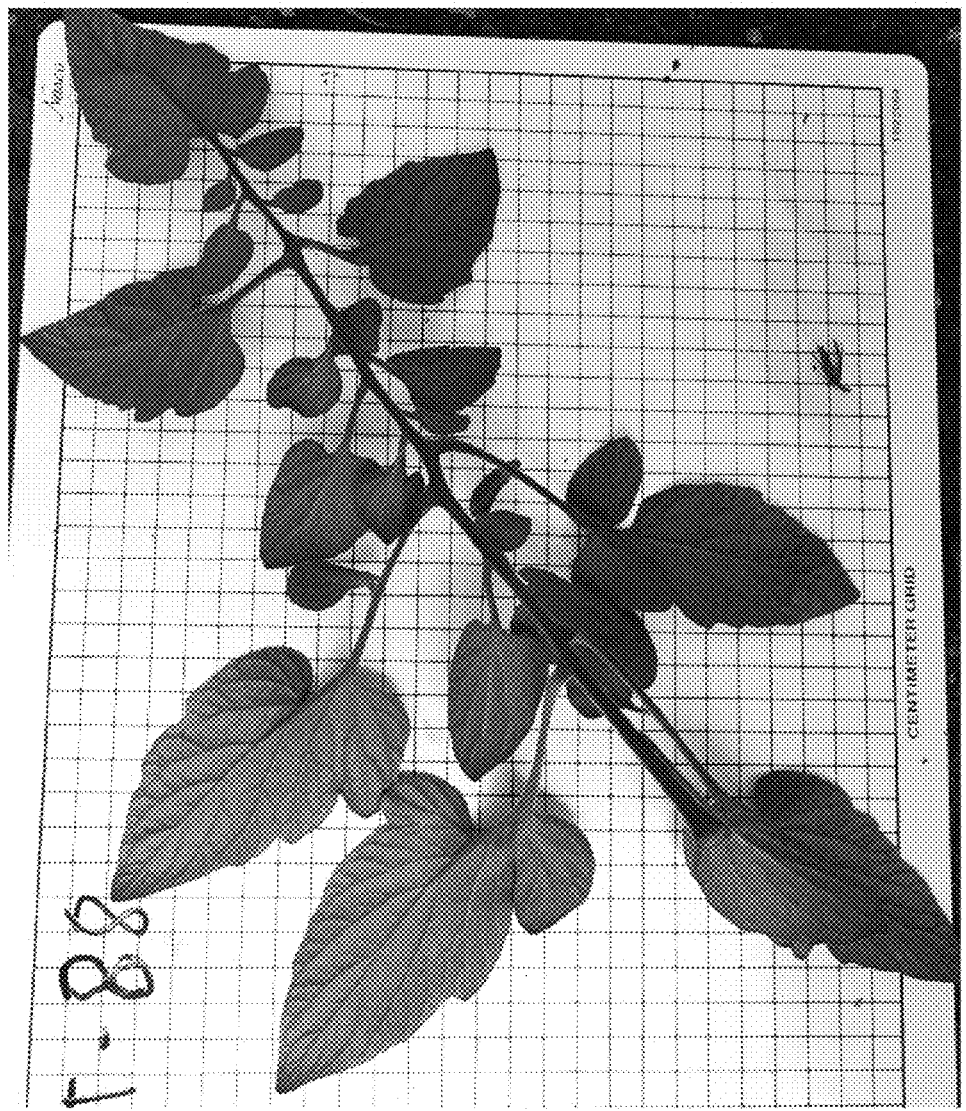
FIG. 2A and FIG. 2B illustrate leaves from the tomato rootstock variety 'RTS-188'.
Figure 2B:
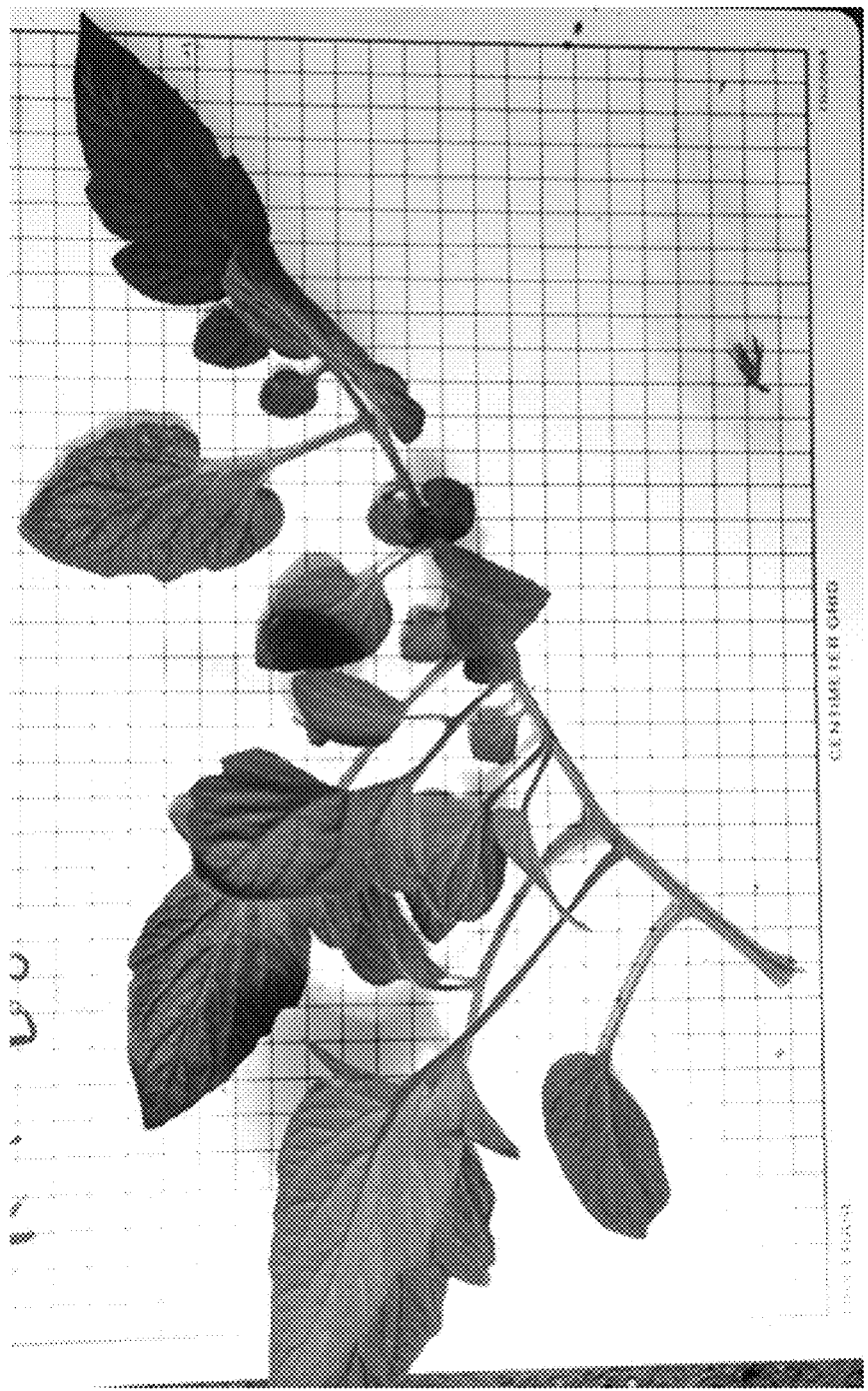
Figure 3:
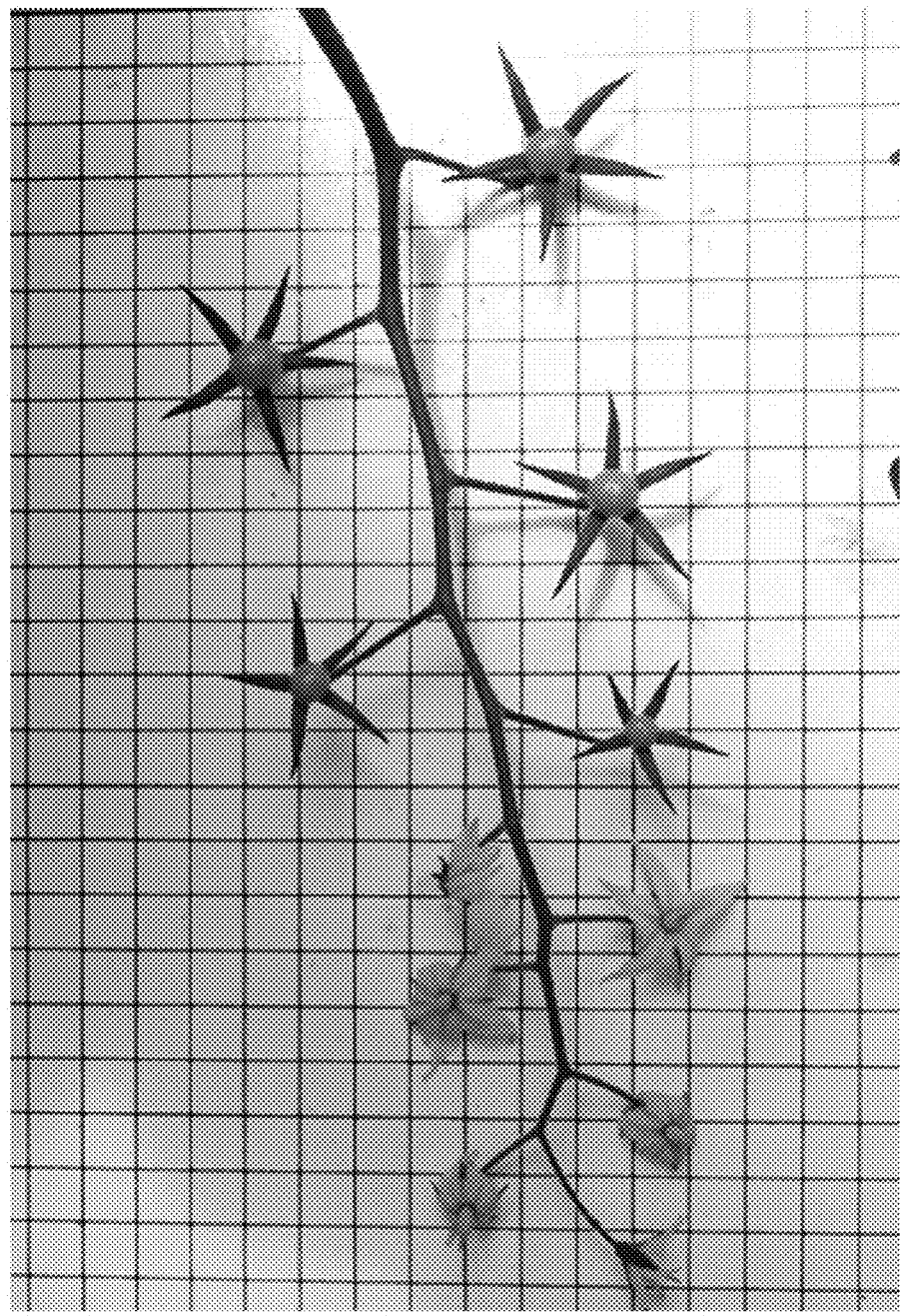
FIG. 3 illustrates inflorescence from the tomato rootstock variety 'RTS-188'. In the photograph, each square on the sheet is 1 cm$^2$.
Figure 4A:
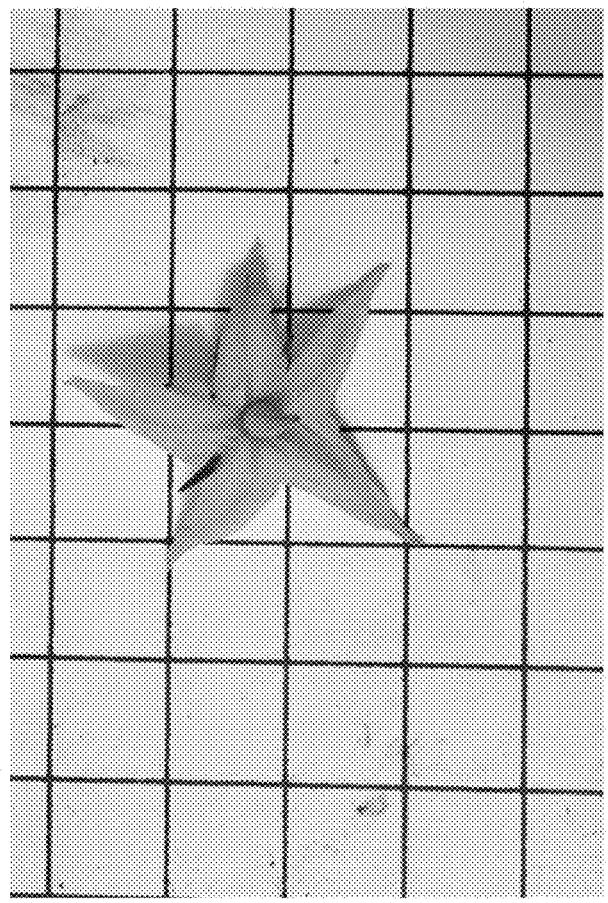
FIG. 4A and FIG. 4B illustrate a flower (anthers: all fused into tube) from the tomato rootstock variety 'RTS-188'. In the photographs, each square on the sheet is 1 cm$^2$.
Figure 4B:
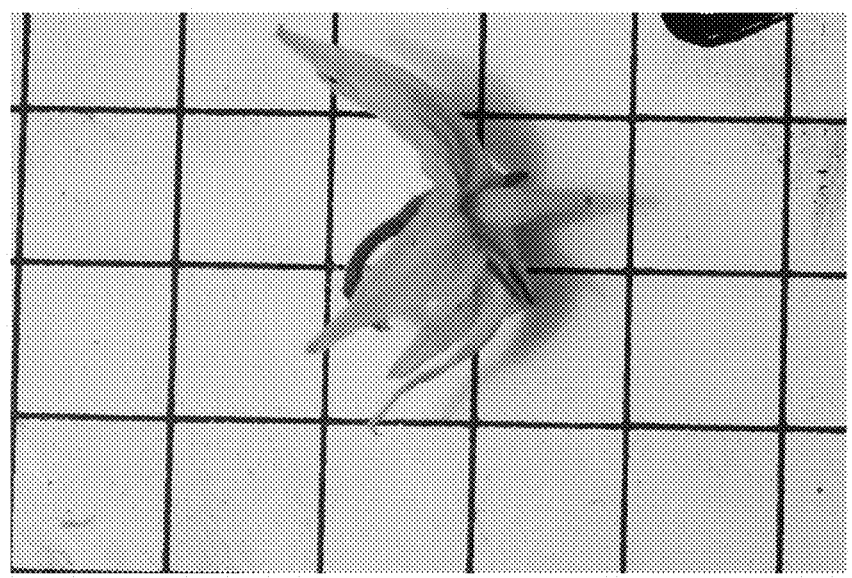
Figure 5:
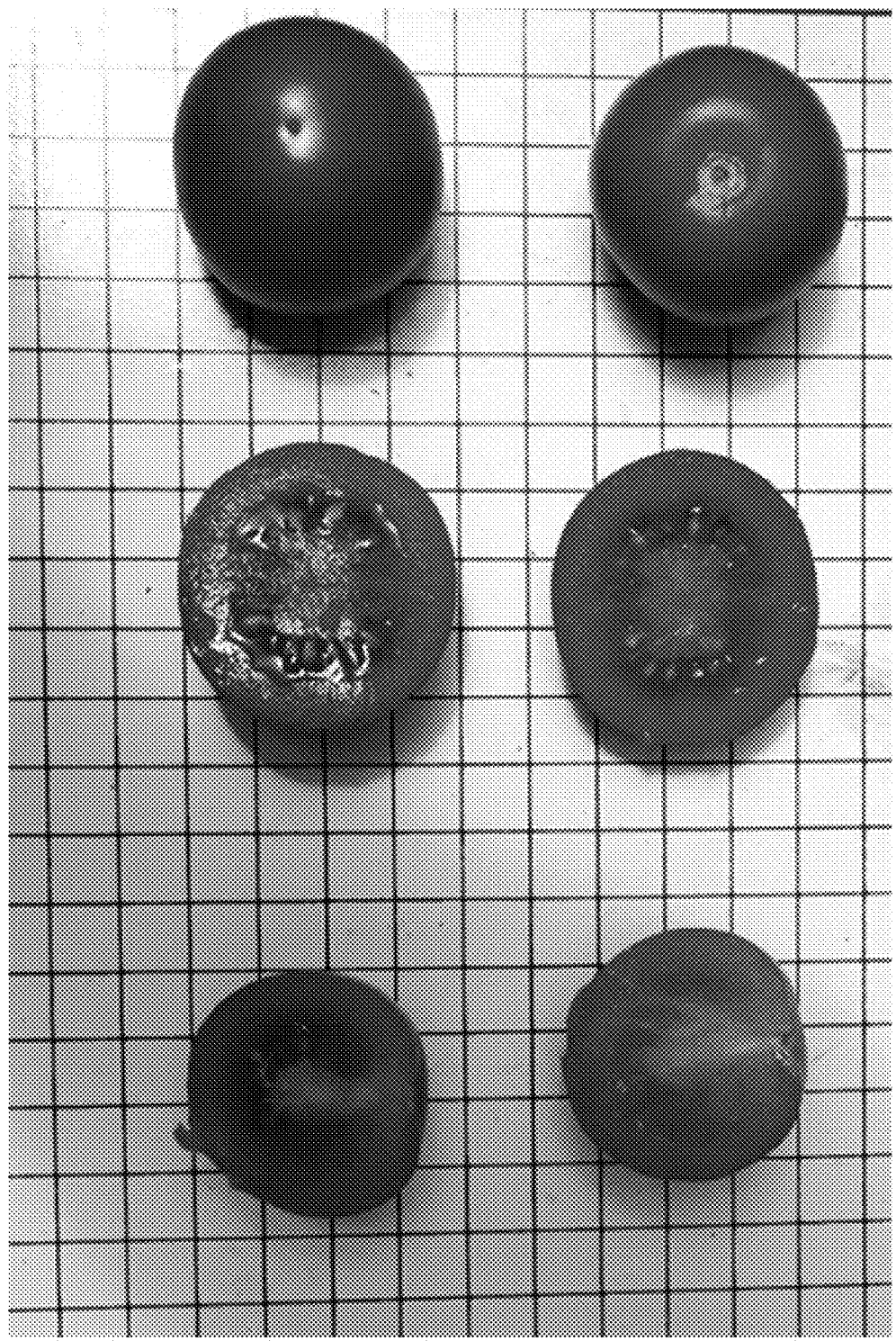
FIG. 5 illustrates fruit from the tomato rootstock variety 'RTS-188' and cross sections of fruit from the tomato rootstock variety 'RTS-188'. In the photograph, each square on the sheets is 1 cm$^2$.

Characterization of Tomato Rootstock Variety 'RTS-188'
Seedling
Anthocyanin in hypocotyl of 2-15 cm seedling: Present
Hypocotyl: Strong and long
Habit of 3-4 week old seedling: Tall
Mature Plant
FIG. 1 is a photograph of a representative plant of tomato rootstock variety 'RTS-188'.
Average height (in cm): 250 cm
Growth: Indeterminate
Form: Normal
Size of canopy (compared to others of similar type): Medium
Habit: Sprawling
Stem
Average length (in cm): 250 cm
Branching: Intermediate
Branching at cotyledonary or first leafy node: Present
Number of nodes between first inflorescence: 10
Number of nodes between early (1st-2nd, 2nd-3rd) inflorescences: 3
Number of nodes between later developing inflorescences: 3
Pubescence on younger stems: Smooth Leaf (Mature Leaf Beneath the 3rd Inflorescence)
FIGS. 2A and 2B are representative photographs showing abaxial and adaxial views, respectively, of leaves of tomato rootstock variety 'RTS-188'.
Type: Tomato
Morphology of mature leaf: Bipinnate
Average length and width (in cm): Length: 25 cm; Width: 25 cm
Margins of major leaflets: Shallowly toothed or scalloped
Marginal rolling or wiltiness: Absent
Onset of leaflet rolling: Early season
Surface of major leaflets: Rugose (bumpy or veiny)
Pubescence: Smooth
Inflorescence (Make Observations on 3rd Inflorescence)
FIG. 3 is a photograph showing characteristic inflorescence of the plant of tomato rootstock variety 'RTS-188'.
Type: Mainly uniparous
Average number of flowers in inflorescence: 12
Leafy or "running" inflorescences: Absent
Flower
FIGS. 4A and 4B are photographs showing characteristic flowers of tomato rootstock variety 'RTS-188'.
Calyx: Normal, lobes awl-shaped
Calyx-lobes: Shorter than the corolla
Corolla color: Yellow
Style pubescence: Absent
Anthers: All fused into tube
Fasciation (1st flower of 2nd or 3rd inflorescence): Absent
Fruit (3rd Fruit of 2nd or 3rd Cluster)
FIG. 5 is a photograph showing characteristic fruit of tomato rootstock variety 'RTS-188'.
Typical fruit shape: Round
Shape of transverse section: Round
Shape of stein end: Normal
Shape of blossom end: Indented
Shape of pistil scar: Round
Abscission layer: Present
Point of detachment of fruit at harvest: At pedicel joint
Average length (in mm) of pedicel (from joint to calyx attachment): 30 mm
Average length (in mm) of mature fruit (stein axis): 30 mm
Average diameter (in mm) of fruit at widest point: 40 mm
Average weight (in g) of mature fruit: 20 g
Number of locules: Two
Fruit surface: Smooth
Fruit base color (mature-green stage): Light green (e.g., 'Lanai', 'VF 145-F5')
Fruit pattern (mature-green stage): Uniform
Fruit color, full-ripe: Red
Flesh color full-ripe: Red
Flesh color: Uniform
Locular gel color of table-ripe fruit: Yellow
Ripening: Outside in
Stem scar size: Small (e.g., 'Roma')
Core: Medium
Epidermis color: Yellow
Epidermis: Normal
Epidermis texture: Average
Thickness of the pericarp: Thick
Phenology
Fruiting season: Long (e.g., 'Marglobe')
Relative maturity in areas tested: Variable
Adaptation
Culture: Open field
Principle use(s): Rootstock
Machine harvest: Adapted
Automated grafting: Adapted Regions to which adaptation has been demonstrated: California: Sacramento and Upper San Joaquin Valley; California: Southern San Joaquin Valley, and deserts.

Pathogen Resistance and/or Tolerance

FIGS. 6A and 6B is a photograph depicting the difference in growth between 'N6415' tomato plants grafted on tomato rootstock variety 'RTS-188' and non-grafted 'N6415'tomato plants grown in a field infected with Fusarium wilt race 3.

Fusarium wilt race 1 resistance and/or tolerance: confers resistance and/or tolerance to grafted tomato plants.

Fusarium wilt race 2 resistance and/or tolerance: confers resistance and/or tolerance to grafted tomato plants.

Fusarium wilt race 3 resistance and/or tolerance: confers resistance and/or tolerance to grafted tomato plants.

Verticillium wilt race 1 resistance and/or tolerance: confers resistance and/or tolerance to grafted tomato plants.

Tobacco mosaic virus (TMV) resistance and/or tolerance: confers resistance and/or tolerance to grafted tomato plants.

Comparison to Most Similar Variety

Table 1 below compares some of the characteristics of tomato rootstock variety 'RTS-188' with similar variety, 'Arnold'. Column 1 lists the characteristics, column 2 shows the characteristics for tomato rootstock variety 'RTS-188', and column 3 shows the characteristics for most similar tomato plant variety 'Arnold'.

TABLE 1

| Characteristic | 'RTS-188' | 'Arnold' |
| --- | --- | --- |
| Time of flowering | Early | Medium |
| Leaf pubescence | Smooth | Hirsute |
| Leaf coverage | Medium | High |
| Seed content | 20-40 | 10-20 |

Further Embodiments

This present disclosure is also directed to methods for producing a tomato plant by crossing a first parent tomato plant with a second parent tomato plant where either the first or second parent tomato plant is a tomato plant of tomato rootstock variety 'RTS-188'. Further, both first and second parent tomato plants can come from a tomato plant of tomato rootstock variety 'RTS-188'. All plants produced using a tomato plant of tomato rootstock variety 'RTS-188' as a parent are within the scope of the disclosure, including plants derived from a tomato plant of tomato rootstock variety 'RTS-188' ('RTS-188'-derived plant). Further, the disclosure is directed to methods for producing a tomato plant derived from a tomato plant of tomato rootstock variety 'RTS-188' by crossing a tomato plant of tomato rootstock variety 'RTS-188' with a second tomato plant and growing the progeny seed, and repeating the crossing and growing steps with the 'RTS-188'-derived plant from 0 to 7 times. Thus, any such methods using a tomato plant of tomato rootstock variety 'RTS-188' are included in this disclosure: selfing, backcrosses, hybrid production, crosses to populations, and the like. Plants produced using a tomato plant of tomato rootstock variety 'RTS-188' as a parent are presented herein, including plants derived from a tomato plant of tomato rootstock variety 'RTS-188'. Advantageously, a tomato plant of tomato rootstock variety 'RTS-188' may be used in crosses with other tomato plants including, for example, other tomato hybrids, to produce first generation ($F_1$) tomato hybrid seeds and plants with superior characteristics.

As used herein, the term plant includes plant cells, plant protoplasts, plant cell tissue cultures from which tomato plants can be regenerated, plant calli, plant clumps and plant cells that are intact in plants or parts of plants, such as embryos, pollen, ovules, flowers, leaves, stems, and the like.

With the advent of molecular biological techniques that have allowed the isolation and characterization of genes that encode specific protein products, scientists in the field of plant biology developed a strong interest in engineering plant genomes to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Several methods for producing transgenic plants have been developed, and the present disclosure, in particular embodiments, also relates to transformed versions of plants. In particular, the present disclosure relates to transformed versions of tomato rootstock variety 'RTS-188'.

Plant transformation involves the construction of an expression vector that will function in plant cells. Such a vector contains DNA including a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed tomato plants using transformation methods as described herein to incorporate transgenes into the genetic material of the tomato plant(s).

Expression Vectors for Transformation of Tomato Rootstock Variety 'RTS-188'

Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. Positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin (Fraley et al., Proc. Natl. Acad. Sci. U.S.A., 80:4803 (1983)). Another commonly used selectable marker gene is the hygromycin phosphotransferase gene which confers resistance to the antibiotic hygromycin (Vanden Elzen et al., Plant Mol. Biol., 5:299 (1985)).

Additional selectable marker genes of bacterial origin that confer resistance to antibiotics include gentamycin acetyl transferase, streptomycin phosphotransferase, aminoglycoside-3'-adenyl transferase, the bleomycin resistance determinant (Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986)). Other selectable marker genes confer resistance to herbicides such as glyphosate, glufosinate or bromoxynil (Comai et al., Nature 317:741-744 (1985), Gordon-Kamm et al., Plant Cell 2:603-618 (1990) and Stalker et al., Science 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., Science 233:478 (1986), Charest et al., Plant Cell Rep. 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include alpha-glucuronidase (GUS), alpha-galactosidase, luciferase and chloramphenicol, acetyltransferase (Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984)).

In vivo methods for visualizing GUS activity that do not require destruction of plant tissues are available (Molecular Probes publication 2908, IMAGENE GREEN, p.1-4 (1993) and Naleway et al., J. Cell Biol. 115:151 a (1991)). More recently, a gene encoding Green Fluorescent Protein (GFP) has been utilized as a marker for gene expression in prokaryotic and eukaryotic cells (Chalfie et al., Science 263:802 (1994)). GFP and mutants of GFP may be used as screenable markers.

Promoters

Genes included in expression vectors may be driven by a nucleotide sequence containing a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include, for example, promoters that preferentially initiate transcription in certain tissues such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include, for example, anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Inducible Promoters: An inducible promoter is operably linked to a gene for expression in tomato. Optionally, the inducible promoter is operably linked to a nucleotide sequence encoding a signal sequence which is operably linked to a gene for expression in tomato. Inducible promoters may regulate transcription in response to an inducing agent.

Any inducible promoter can be used herein. See Ward et al., Plant Mol. Biol. 22:361-366 (1993). Exemplary inducible promoters may include, for example, that from the ACEI system which responds to copper (Mett et al., Proc. Natl. Acad. Sci. U.S.A. 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

Constitutive Promoters: A constitutive promoter is operably linked to a gene for expression in tomato or the constitutive promoter is operably linked to a nucleotide sequence encoding a signal sequence which is operably linked to a gene for expression in tomato.

Many different constitutive promoters can be utilized herein. Exemplary constitutive promoters may include, for example, the promoters from plant viruses such as the 35S promoter from CaMV (Odell et al., Nature 313:810-812 (1985) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3):291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO 96/30530.

Tissue-specific or Tissue-preferred Promoters: A tissue-specific promoter is operably linked to a gene for expression in tomato. Optionally, the tissue-specific promoter is operably linked to a nucleotide sequence encoding a signal sequence which is operably linked to a gene for expression in tomato. Plants transformed with a transgene operably linked to a tissue-specific promoter produce the transgenic protein product exclusively, or preferentially, in a specific tissue.

Any tissue-specific or tissue-preferred promoter can be utilized herein. Exemplary tissue-specific or tissue-preferred promoters may include, for example, a root-preferred promoter, such as that from the phaseolin gene (Mural et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

The present disclosure further relates to transformed versions of tomato rootstock variety RTS-188' comprising a vector useful for targeting proteins to subcellular compartments using tissue specific promotors. Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon et al., Cell 39:499-509 (1984), Steifel et al., Plant Cell 2:785-793 (1990).

Foreign Protein Genes and Agronomic Genes

With transgenic plants of tomato rootstock variety 'RTS-188' according to the present disclosure, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and On, Anal. Biochem. 114:92-6 (1981).

According to a preferred embodiment, the transgenic plant provided for commercial production of foreign protein is a tomato plant. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology, CRC Press, Boca Raton 269:284 (1993). Map information concerning chromosomal location is useful, for example, in genetic comparisons where the genetic maps of two plants are compared. Wang et al. discuss "Large Scale Identification, Mapping and Genotyping of Single-Nucleotide Polymorphisms in the Human Genome," Science, 280: 1077-1082, 1998, and similar capabilities are becoming increasingly available for the tomato genome. Map comparisons may involve, for example, hybridizations, RFLP, PCR, SSR and sequencing, all of which are conventional techniques. SNPs may also be used alone or in combination with other techniques.

Likewise, by means of the present disclosure, plants can be genetically engineered to express various phenotypes of horticultural interest. Through the transformation of tomato the expression of genes can be altered to enhance disease resistance, insect resistance, herbicide resistance, horticultural quality and other traits. Transformation can also be used to insert DNA sequences which control or help control male-sterility. DNA sequences native to tomato as well as non-native DNA sequences can be transformed into tomato and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including, for example, knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12: 883-888; and Neuhuber et al. (1994) Mol. Gen. Genet. 244:230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507), virus-induced gene silencing (Burton, et al. (2000) Plant Cell 12:691-705; and Baulcombe (1999) Curr. Op. Plant Bio. 2:109-113); target-RNA-specific ribozymes (Haseloff et al. (1988) Nature 334: 585-591); hairpin structures (Smith et al. (2000) Nature 407:319-320; WO 99/53050; and WO 98/53083); MicroRNA (Aukerman & Sakai (2003) Plant Cell 15:2730-2741); ribozymes (Steinecke et al. (1992) EMBO J. 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present disclosure, other genes can be expressed in transformed plants, such as transformed versions of a tomato plant of tomato rootstock variety 'RTS-188'. More particularly, plants can be genetically engineered to express various phenotypes of interest. Exemplary genes implicated in this regard may include, for example, those categorized below.

Genes that Confer Resistance to Pests or Disease

Plant disease resistance genes: Plant defenses are often activated by specific interaction between the product of a disease resistance gene (R) in the plant and the product of a corresponding avirulence (Avr) gene in the pathogen. A plant variety, such as a tomato variety, can be transformed with one or more cloned resistance genes to engineer plants that are resistant to specific pathogen strains. See, for example, Jones et al., Science 266:789 (1994) (cloning of the tomato Cf-9 gene for resistance to *Cladosporium fulvum*); Martin et al., Science 262:1432 (1993) (tomato Pto gene for resistance to Pseudomonas syringae pv. tomato encodes a protein kinase); Mindrinos et al. Cell 78:1089 (1994) (Arabidopsis RSP2 gene for resistance to Pseudomonas syringae), McDowell & Woffenden, (2003) Trends Biotechnol. 21(4): 178-83 and Toyoda et al., (2002) Transgenic Res. 11 (6):567-82.

A gene conferring resistance to a pest, such as a nematode: See, for example, PCT Application WO 96/30517; PCT Application WO 93/19181.

A *Bacillus thuringiensis* protein, a derivative thereof or a synthetic polypeptide modeled thereon: See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

A lectin: See, for example, Van Damme et al., Plant Molec. Biol. 24:25 (1994), who disclose the nucleotide sequences of several *Clivia miniata* mannose-binding lectin genes.

A vitamin-binding protein, such as avidin: See, for example, PCT application US 93/06487 which teaches the use of avidin and avidin homologues as larvicides against insect pests.

An enzyme inhibitor, for example, a protease or proteinase inhibitor or an amylase inhibitor: See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

An insect-specific hormone or pheromone such as an ecdysteroid or juvenile hormone, a variant thereof, a mimetic based thereon, or an antagonist or agonist thereof: See, for example, the disclosure by Hammock et al., Nature 344:458 (1990), of baculovirus expression of cloned juvenile hormone esterase, an inactivator of juvenile hormone.

An insect-specific peptide or neuropeptide which, upon expression, disrupts the physiology of the affected pest: For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., which discloses genes encoding insect-specific, paralytic neurotoxins.

An insect-specific venom produced in nature by a snake, a wasp, etc. For example, see Pang et al., Gene 116:165 (1992), for disclosure of heterologous expression in plants of a gene coding for a scorpion insectotoxic peptide.

An enzyme responsible for hyperaccumulation of a monoterpene, a sesquiterpene, a steroid, hydroxamic acid, a phenylpropanoid derivative or another non-protein molecule with insecticidal activity.

An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic: See, for example, PCT application WO 93/02197 (Scott et al.), which discloses the nucleotide sequence of a callase gene. DNA molecules which contain chitinase-encoding sequences can be obtained from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene, U.S. Pat. Nos. 7,145,060, 7,087,810 and 6,563,020.

A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

A hydrophobic moment peptide: See, for example, PCT application WO 95/16776 and U.S. Pat. No. 5,580,852, which disclose peptide derivatives of tachyplesin which inhibit fungal plant pathogens, and PCT application WO 95/18855 and U.S. Pat. No. 5,607,914 which teaches synthetic antimicrobial peptides that confer disease resistance.

A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to *Pseudomonas solanacearum*.

A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus and tobacco mosaic virus.

An insect-specific antibody or an immunotoxin derived therefrom. Thus, an antibody targeted to a critical metabolic function in the insect gut would inactivate an affected enzyme, killing the insect. See, for example, Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

A virus-specific antibody: See, for example, Tavladoraki et al., Nature 366:469 (1993), who show that transgenic plants expressing recombinant antibody genes are protected from virus attack.

A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, for example, Lamb et al., Bio/Technology 10:1436 (1992). The cloning and characterization of a gene which encodes a bean endopolygalacturonase-inhibiting protein is described by Toubart et al., Plant J. 2:367 (1992).

A developmental-arrestive protein produced in nature by a plant. For example, Logemann et al., Bio/Technology 10:305 (1992), have shown that transgenic plants expressing the barley ribosome-inactivating gene have an increased resistance to fungal disease.

Genes involved in the Systemic Acquired Resistance (SAR) Response and/or the pathogenesis-related genes. For example, see Briggs, S., Current Biology, 5(2) (1995); Pieterse & Van Loon (2004) Curr. Opin. Plant Bio. 7(4): 456-64 and Somssich (2003) Cell 113(7):815-6.

Antifungal genes: See Cornelissen and Melchers, Plant Physiol., 101:709-712 (1993); Parijs et al., Planta 183:258-264 (1991) and Bushnell et al., Can. J. of Plant Path. 20(2):137-149 (1998). Also see U.S. Pat. No. 6,875,907.

Detoxification genes, such as for fumonisin, beauvericin, moniliformin and zearalenone and their structurally related derivatives. For example, see U.S. Pat. No. 5,792,931.

Cystatin and cysteine proteinase inhibitors: See, for example, U.S. Pat. No. 7,205,453.

Defensin genes: See, for example, WO 03/000863 and U.S. Pat. No. 6,911,577.

Genes conferring resistance to nematodes: See, for example, PCT Application WO 96/30517; PCT Application WO 93/19181, WO 03/033651 and Urwin et al., Planta 204:472-479 (1998), Williamson (1999) Curr Opin Plant Bio. 2(4):327-31.

Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

Genes that confer resistance to Brown Stem Rot: See, for example, those described in U.S. Pat. No. 5,689,035.

Genes that Confer Resistance to an Herbicide

An herbicide that inhibits the growing point or meristem, such as an imidazolinone or a sulfonylurea: See, for example, exemplary genes in this category that code for mutant ALS and AHAS enzyme as described by Lee et al., EMBO J. 7:1241 (1988), and Miki et al., *Theor. Appl. Genet.* 80:449 (1990), respectively.

Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexanediones (ACCase inhibitor-encoding genes): See, for example, U.S. Pat. No. 4,940,835 to Shah, et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications EP1173580; WO 01/66704; EP1173581 and EP1173582. Glyphosate resistance is also imparted to plants that express a gene that encodes a glyphosate oxido-reductase enzyme as described more fully in U.S. Pat. Nos. 5,776,760 and 5,463,175. In addition glyphosate resistance can be imparted to plants by the over expression of genes encoding glyphosate N-acetyltransferase. See, for example, U.S. application Ser. No. 10/427, 692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., Theor. Appl Genet. 83:435 (1992).

An herbicide that inhibits photosynthesis, such as a triazine (psbA and gs+genes) and a benzonitrile (nitrilase gene): See, for example, Przibila et al., Plant Cell 3:169 (1991), describe the transformation of Chlamydomonas with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

Acetohydroxy acid synthase, which has been found to make plants that express this enzyme resistant to multiple types of herbicides, has been introduced into a variety of plants. See, for example, Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

Protoporphyrinogen oxidase (protox) is necessary for the production of chlorophyll. The protox enzyme serves as the target for a variety of herbicidal compounds. These herbicides also inhibit growth of different species of plants present. The development of plants containing altered protox activity which are resistant to these herbicides are described in, for example, U.S. Pat. Nos. 6,288,306; 6,282, 837; 5,767,373; and international publication WO 01/12825.

Genes that Confer or Contribute to a Value-Added Trait

Modified fatty acid metabolism, for example, by transforming a plant with an antisense gene of stearyl-ACP desaturase to increase stearic acid content of the plant. See, for example, Knultzon et al., Proc. Natl. Acad. Sci. USA 89:2625 (1992).

Decreased phytate content: 1) Introduction of a phytase-encoding gene enhances breakdown of phytate, adding more free phosphate to the transformed plant. For example, see Van Hartingsveldt et al., Gene 127:87 (1993), for a disclosure of the nucleotide sequence of an Aspergillus niger phytase gene. 2) Up-regulation of a gene that reduces phytate content. This, for example, could be accomplished by cloning and then re-introducing DNA associated with one or more of the alleles, such as the LPA alleles, identified in maize mutants characterized by low levels of phytic acid, such as in Raboy et al., Maydica 35: 383 (1990) and/or by altering inositol kinase activity as in WO 02/059324, US2003/0009011, WO 03/027243, US2003/0079247, WO 99/05298, U.S. Pat. Nos. 6,197,561, 6,291,224, 6,391,348, WO 2002/059324, U.S. Pat. No. 2003/0079247, WO98/45448, WO99/55882, WO01/04147.

Impacting carbohydrate compositions by, for example, transforming plants with a gene coding for an enzyme that alters the branching pattern of starch, or a gene altering thioredoxin such as NTR and/or TRX (See U.S. Pat. No. 6,531,648) and/or a gamma zein knock out or mutant such as cs27 or TUSC27 or en27 (See U.S. Pat. No. 6,858,778 and US2005/0160488, US2005/0204418). See Shiroza et al., J. Bacteriol. 170: 810 (1988) (nucleotide sequence of Streptococcus mutans fructosyltransferase gene), Steinmetz et al., Mol. Gen. Genet. 200: 220 (1985) (nucleotide sequence of Bacillus subtilis levansucrase gene), Pen et al., Bio/Technology 10: 292 (1992) (production of transgenic plants that express Bacillus licheniformis alpha-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley alpha-amylase gene), and Fisher et al., Plant Physiol.

102: 1045 (1993) (maize endosperm starch branching enzyme II), WO 99/10498 (improved digestibility and/or starch extraction through modification of UDP-D-xylose 4-epimerase, Fragile 1 and 2, Ref 1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

Altered antioxidant content or composition, such as alteration of tocopherol or tocotrienols: For example, see U.S. Pat. Nos. 6,787,683 and 7,154,029 and WO 00/68393 involving the manipulation of antioxidant levels through alteration of a phytl prenyl transferase (ppt), WO 03/082899 through alteration of a homogentisate geranyl transferase (hggt).

Genes that Control Male Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

Introduction of a deacetylase gene under the control of a tapetum-specific promoter and with the application of the chemical N—Ac-PPT: See, for example, international publication WO 01/29237.

Introduction of various stamen-specific promoters: See, for example, international publications WO 92/13956 and WO 92/13957.

Introduction of the barnase and the barstar genes: See, for example, Paul et al., Plant Mol. Biol. 19:611-622, 1992).

For additional examples of nuclear male and female sterility systems and genes, see also, U.S. Pat. Nos. 5,859, 341; 6,297,426; 5,478,369; 5,824,524; 5,850,014; and 6,265,640.

Genes that Create a Site for Site Specific DNA Integration

Genes that confer resistance to Brown Stem Rot: See, for example, those described in U.S. Pat. No. 5,689,035.Introduction of FRT sites that may be used in the FLP/FRT system and/or Lox sites that may be used in the Cre/Loxp system for site-specific DNA integration. For example, see Lyznik, et al., Site-Specific Recombination for Genetic Engineering in Plants, Plant Cell Rep (2003) 21:925-932 and WO 99/25821. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

Genes that Affect Abiotic Stress Resistance

Genes that affect abiotic stress resistance (including, for example, flowering and fruit development, drought resistance or tolerance, cold resistance or tolerance, and salt resistance or tolerance) and increased yield under stress: For example, see: WO 00/73475 where water use efficiency is altered through alteration of malate; U.S. Pat. Nos. 5,892, 009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other desirable traits; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/ 052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 20040098764 or US 20040078852.

Other genes and transcription factors that affect plant growth and other traits, such as yield, flowering, plant growth and/or plant structure, can be introduced or introgressed into plants. See, for example, WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29,123 U.S. Pat. Nos. 6,794,560, 6,307,126 (GAI), WO 99/09174 (D8 and Rht), and WO 2004/076638 and WO 2004/031349 (transcription factors).

Methods for Transformation of Tomato Plants of Tomato Rootstock Variety 'RTS-188'

Numerous methods for plant transformation have been developed including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

Agrobacterium-mediated Transformation: One method for introducing an expression vector into plants is based on the natural transformation system of Agrobacterium. See, for example, Horsch et al., Science 227:1229 (1985). A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. See, for example, Kado, C. I., Crit. Rev. Plant Sci. 10:1 (1991). Descriptions of Agrobacterium vector systems and methods for Agrobacterium-mediated gene transfer are provided by Gruber et al., supra, Miki et al., supra and Moloney et al., Plant Cell Reports 8:238 (1989). See also, U.S. Pat. No. 5,563,055 (Townsend and Thomas), issued Oct. 8, 1996.

Direct Gene Transfer: Alternatives to Agrobacterium-mediated transformation exist such as, for example, direct gene transfer. A generally applicable method of plant transformation is microprojectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987); Sanford, J. C., Trends Biotech. 6:299 (1988); Klein et al., Bio/Tech. 6:559-563 (1988); Sanford, J. C. Physiol Plant 7:206 (1990); Klein et al., Biotechnology 10:268 (1992). See also U.S. Pat. No. 5,015,580 (Christou et al.), issued May 14, 1991 and U.S. Pat. No. 5,322,783 (Tomes, et al.), issued Jun. 21, 1994.

Another method for physical delivery of DNA to plants is sonication of target cells. See, for example, Zhang et al., Bio/Technology 9:996 (1991). Alternatively, liposome and spheroplast fusion have been used to introduce expression vectors into plants. Deshayes et al., EMBO J., 4:2731 (1985); Christou et al., Proc Natl. Acad. Sci. USA 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994)).

Following transformation of target tomato tissues, expression of the above-described selectable marker genes allows for preferential selection of transformed cells, tissues and/or plants, using regeneration and selection methods well known in the art.

The foregoing methods for transformation may be used for producing a transgenic variety are merely exemplary. One of skill in the art may recognize additional transformation techniques that may be used to produce new tomato varieties described herein. A transgenic variety may be crossed with another (non-transformed or transformed) variety in order to produce a new transgenic variety. Alternatively, a genetic trait that has been engineered into a particular tomato line could be moved into another line using traditional backcrossing techniques that are well known in the plant breeding arts. For example, a backcrossing approach could be used to move an engineered trait from a public variety into a desirable hybrid, or from a variety containing a foreign gene in its genome into a variety or varieties that do not contain that gene. As used herein, "crossing" can refer to a simple X by Y cross or the process of backcros sing, depending on the context.

Genetic Marker Profile Through SSR and First Generation Progeny

In addition to phenotypic observations, a plant, for example a plant of tomato rootstock variety 'RTS-188', can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" Crop Science 39:1464-1490 (1999), and Berry et al., Assessing Probability of Ancestry Using Simple Sequence Repeat Profiles: Applications to Maize Inbred Lines and Soybean Varieties" Genetics 165:331-342 (2003).

Particular markers used for these purposes may include any type of marker and marker profile which provides a means of distinguishing varieties. One method of comparison is to use only homozygous loci for a tomato plant of tomato rootstock variety 'RTS-188'.

Primers and PCR protocols for assaying these and other markers are known in the art and may be adapted from those disclosed in the Soybase (sponsored by the USDA Agricultural Research Service and Iowa State University). In addition to being used for identification of tomato plants of tomato rootstock variety 'RTS-188' and plant parts and plant cells of tomato plants of tomato rootstock variety 'RTS-188', the genetic profile may be used to identify a tomato plant produced through the use of a tomato plant of tomato rootstock variety 'RTS-188' or to verify a pedigree for progeny plants produced through the use of a tomato plant of tomato rootstock variety 'RTS-188'. The present disclosure relates to a tomato variety characterized by molecular and physiological data obtained from the representative sample of said variety deposited with the American Type Culture Collection (ATCC). Further provided by the disclosure is a tomato plant formed by the combination of one of the disclosed tomato plants or plant cells with another tomato plant or cell and containing the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be informative in linkage analysis relative to other marker systems in that multiple alleles may be present. Another advantage of this type of marker is that, through use of flanking primers, detection of SSRs can be achieved, for example, by the polymerase chain reaction (PCR). The PCR detection involves the use of two oligonucleotide primers flanking the polymorphic segment of repetitive DNA, repeated cycles of heat denaturation of the DNA followed by primer annealing to complementary sequences at low temperatures, and extension of the annealed primers with DNA polymerase. Following amplification, markers can be scored by electrophoresis of the amplification products. Scoring of marker genotype is based on the size of the amplified fragment, which may be measured by the number of base pairs of the fragment.

The SSR profile of tomato variety such as a tomato plant of tomato rootstock variety 'RTS-188' can be used to identify tomato plants having that tomato variety as a parent, since such progeny tomato plants will contain the same homozygous alleles as the parent. For tomato varieties that are essentially homozygous at all relevant loci, most loci should have only one type of allele present. In contrast, a genetic marker profile of an F1 progeny should be the sum of those parents, e.g., if one parent was homozygous for allele x at a particular locus, and the other parent homozygous for allele y at that locus, then the F1 progeny will be xy (heterozygous) at that locus. Subsequent generations of progeny produced by selection and breeding are expected to be of genotype x (homozygous), y (homozygous), or xy (heterozygous) for that locus position. When the F1 plant is selfed or sibbed for successive filial generations, the locus should be either x or y for that position.

In addition, plants and plant parts substantially benefiting from the use of a tomato plant of tomato rootstock variety 'RTS-188' containing a backcross conversion, transgene, or genetic sterility factor, may be identified by having a molecular marker profile with a high percent identity to a tomato plant of tomato rootstock variety 'RTS-188' used in their development. Such a percent identity might be 95%, 96%, 97%, 98%, 99%, 99.5% or 99.9% identical to a tomato plant of tomato rootstock variety 'RTS-188' used to develop the plant and/or plant part.

The SSR profile of a tomato plant of tomato rootstock variety 'RTS-188' can also be used to identify essentially derived varieties and other progeny varieties developed from the use of a tomato plant of tomato rootstock variety 'RTS-188', as well as cells and other plant parts thereof. Such plants may be developed using the markers identified in WO 00/31964, U.S. Pat. No. 6,162,967 and U.S. application Ser. No. 09/954,773. Progeny plants and plant parts produced using a tomato plant of tomato rootstock variety 'RTS-188' may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from a tomato plant of tomato rootstock variety 'RTS-188', as measured by either percent identity or percent similarity. Such progeny may be further characterized as being within a pedigree distance of respective tomato plant, such as within 1, 2, 3, 4 or 5 or less cross-pollinations to a tomato plant other than a tomato plant of tomato rootstock variety 'RTS-188' or a plant that has a tomato plant of tomato rootstock variety 'RTS-188', as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an F1 progeny produced from such variety, and progeny produced from such variety.

Single-Gene Conversions

When the term "tomato plant" is used in the context of the present disclosure, this also includes any single gene conversions of the tomato rootstock variety 'RTS-188'. The term single gene converted plant as used herein refers to those tomato plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present disclosure to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental tomato plant that contributes the gene for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol (Poehlman & Sleper, 1994; Fehr, Principles of Cultivar Development pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a tomato plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add an agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic; examples of these traits include, for example, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445.

Tissue Culture

Further reproduction of tomato rootstock variety 'RTS-188' can occur by tissue culture and regeneration. Tissue culture of various tissues of tomatoes and regeneration of plants therefrom is well known and widely published. For example, reference may be had to Girish-Chandel et al., Advances in Plant Sciences, 2000, 13: 1, 11-17; Costa et al., Plant Cell Report, 2000, 19: 3 327-332; Plastira et al., Acta Horticulturae, 1997, 447, 231-234; Zagorska et al., Plant Cell Report, 1998, 17: 12 968-973; Asahura et al., Breeding Science, 1995, 45: 455-459; Chen et al., Breeding Science, 1994, 44: 3, 257-262, Patil et al., Plant and Tissue and Organ Culture, 1994, 36: 2, 255-258; Gill, R., et al., Somatic Embryogenesis and Plant Regeneration from Seedling Cultures of Tomato (*Lycopersicon esculentum* Mill.), J. Plant Physiol., 147:273-276 (1995); Jose M. Segui-Simarro and Fernando Nuez, Embryogenesis induction, callogenesis, and plant regeneration by in vitro culture of tomato isolated microspores and whole anthers J. Exp. Bot., March 2007; 58: 1119-1132; Hamza et al., Re-evaluation of Conditions for Plant Regeneration and Agrobacterium-Mediated Transformation from Tomato (*Lycopersicon esculentum*), J. Exp. Bot., December 1993; 44: 1837-1845. Thus, another aspect of this disclosure is to provide cells which upon growth and differentiation produce tomato plants having the physiological and morphological characteristics of a tomato plant of tomato rootstock variety 'RTS-188'.

As used herein, the term "tissue culture" indicates a composition containing isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, fruit, petioles, leaves, stems, roots, root tips, anthers, pistils and the like. Means for preparing and maintaining plant tissue culture are well known in the art. By way of example, a tissue culture containing organs has been used to produce regenerated plants. U.S. Pat. Nos. 5,959,185; 5,973,234 and 5,977,445 describe certain techniques.

Vegetative Propagation

Tomato plants can also be propagated vegetatively. Accordingly, the present disclosure is further directed to vegetative propagation of a tomato plant of tomato rootstock variety 'RTS-188'. A part of the plant, for example a shoot tissue, is collected and a new plant is obtained from the part. Such part typically includes an apical meristem of the plant. The collected part is transferred to a medium allowing development of a plantlet including, for example, rooting or development of shoots, or is grafted onto a tomato plant or a rootstock prepared to support growth of shoot tissue. This is achieved using methods well-known in the art. Accordingly, in one embodiment, a method of vegetatively propagating a tomato plant of the present disclosure involves collecting a part of a plant according to the present disclosure, e.g. a shoot tissue, and obtaining a plantlet from said part. In one embodiment, a method of vegetatively propagating a tomato plant of the present disclosure involves: a) collecting tissue of a plant of the present disclosure; and b) rooting said proliferated shoots to obtain rooted plantlets. In one embodiment, a method of vegetatively propagating a plant of the present disclosure involves: a) collecting tissue of a plant of the present disclosure; b) cultivating said tissue to obtain proliferated shoots; and c) rooting said proliferated shoots to obtain rooted plantlets. In one embodiment, such methods further involve growing a plant from said plantlets. In one embodiment, a fruit is harvested from said plant.

Additional Breeding Methods

Tomato varieties, such as tomato rootstock variety 'RTS-188', are typically developed for use as fresh produce or for processing. However, tomato varieties also provide a source of breeding material that may be used to develop new tomato varieties. Plant breeding techniques known in the art and used in a tomato plant breeding program may include, for example, chasing selfs, recurrent selection, mass selection, bulk selection, mutation breeding, backcrossing, pedigree breeding, open pollination breeding, restriction fragment length polymorphism enhanced selection, genetic marker enhanced selection, making double haploids, and transformation. Often combinations of these techniques are used. The development of tomato varieties in a plant breeding program involves, in general, the development and evaluation of homozygous varieties. There are many analytical methods available to evaluate a new variety. The oldest and most traditional method of analysis is the observation of phenotypic traits but genotypic analysis may also be used. Thus, another aspect of the disclosure is to provide a tomato plant of the tomato rootstock variety 'RTS-188' as a source of breeding material for the development of new tomato varieties using, for example, the breeding techniques described herein. One of skill in the art would recognize that additional breeding techniques may exist and may be used to develop new tomato varieties using plants of the tomato rootstock variety 'RTS-188'.

The present disclosure is directed to methods for producing a tomato plant by crossing a first parent tomato plant with a second parent tomato plant where either the first or second parent tomato plant is a tomato plant of tomato rootstock variety 'RTS-188'. The other parent may be any other tomato plant, such as a tomato plant that is part of a synthetic or natural population. Any such methods using a tomato plant of tomato rootstock variety 'RTS-188' are part of this disclosure: selfing, sibbing, backcrosses, mass selection, pedigree breeding, bulk selection, hybrid production, crosses to populations, and the like. These methods are well known in the art and some of the more commonly used breeding methods are described herein. Descriptions of breeding methods can be found in one of several reference books (e.g., Allard, Principles of Plant Breeding, 1960; Simmonds, Principles of Crop Improvement, 1979; Sneep et al., 1979; Fehr, "Breeding Methods for Cultivar Development," 2.sup.nd ed., Wilcox editor, 1987).

The following describes breeding methods that may be used with tomato plants of the tomato rootstock variety 'RTS-188' in the development of further tomato plants. One such embodiment is a method for developing a progeny tomato plant of tomato rootstock variety 'RTS-188' in a tomato plant breeding program involving: obtaining the tomato plant, or a part thereof, of tomato rootstock variety 'RTS-188', utilizing said plant or plant part as a source of breeding material, and selecting a progeny plant of tomato rootstock variety 'RTS-188' with molecular markers in common with tomato rootstock variety 'RTS-188' and/or with morphological and/or physiological characteristics selected from the characteristics disclosed herein in the section entitled "Characterization of Tomato Rootstock Variety 'RTS-188'". Breeding steps that may be used in the tomato plant breeding programs may include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of tomato rootstock variety 'RTS-188' progeny tomato plants, involving crossing a tomato plant of tomato rootstock variety 'RTS-188' with another tomato plant, thereby producing a population of tomato plants, which, on average, derive 50% of their alleles from a tomato plant of tomato rootstock variety 'RTS-188'. A plant of this population may be selected and repeatedly selfed or sibbed with a tomato cultivar resulting from these successive filial generations. In one embodiment, the tomato cultivar produced by this method has obtained at least 50% of its alleles from a tomato plant of tomato rootstock variety 'RTS-188'.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus, the disclosure includes 'RTS-188' progeny tomato plants containing a combination of at least two traits of a tomato plant of tomato rootstock variety 'RTS-188', the traits being selected from those listed in the section entitled "Characterization of Tomato Rootstock Variety 'RTS-188'", so that the progeny tomato plant is not significantly different for the traits than a tomato plant of tomato rootstock variety 'RTS-188' as determined at the 5% significance level when grown in the same environmental conditions. Using techniques described herein, molecular markers may be used to identify said progeny plant as a tomato rootstock variety 'RTS-188' progeny plant. For each of the evaluation schemes involving a tomato plant of tomato rootstock variety 'RTS-188', mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of a tomato plant of tomato rootstock variety 'RTS-188' may also be characterized through their filial relationship with a tomato plant of tomato rootstock variety 'RTS-188', as for example being within a certain number of breeding crosses to a tomato plant of tomato rootstock variety 'RTS-188'. A breeding cross is a cross made to introduce new genetics into the progeny, and is distinguished from a cross, such as a self or a sib cross, made to select among existing genetic alleles. The lower the number of breeding crosses in the pedigree, the closer the relationship between a tomato plant of tomato rootstock variety 'RTS-188' and its progeny. For example, progeny produced by the methods described herein may be within 1, 2, 3, 4 or 5 breeding crosses of a tomato plant of tomato rootstock variety 'RTS-188'

Exemplary breeding techniques are further described herein and may be used in breeding schemes using tomato plants of tomato rootstock variety 'RTS-188'.

Chasing Selfs

Chasing selfs involves identifying inbred plants among tomato plants that have been grown from tomato plant seed, such as the seed from a plant of tomato rootstock variety 'RTS-188'. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present disclosure relates to a method for producing an inbred tomato variety by: planting seed of a tomato plant of tomato rootstock variety 'RTS-188'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato rootstock variety 'RTS-188'. Tomato plants capable of expressing essentially all of the physiological and morphological characteristics of the parental inbred lines of tomato plants of the tomato rootstock variety 'RTS-188' include tomato plants obtained by chasing selfs from seed of a tomato plant of tomato rootstock variety 'RTS-188'.

One of ordinary skill in the art will recognize that once a breeder has obtained inbred tomato plants by chasing selfs from seed of plants of the tomato rootstock variety 'RTS-188', the breeder can then produce new inbred plants such as by sib-pollinating, or by crossing one of the identified inbred tomato plant with a tomato plant of tomato rootstock variety 'RTS-188'.

Backcross Conversion

Tomato plants of the tomato rootstock variety 'RTS-188' represents a new base genetic variety into which a new locus or trait may be introgressed. Backcrossing represents an important method that can be used to accomplish such an introgression. The term backcross conversion and single locus conversion are used interchangeably to designate the product of a backcrossing program.

A backcross conversion of a tomato variety such as, for example, tomato rootstock variety 'RTS-188', occurs when DNA sequences are introduced through backcrossing (Hallauer et al, 1988, "Corn Breeding" Corn and Corn Improvements, No. 18, pp. 463-481), with the tomato variety utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. Desired traits that may be transferred through backcross conversion may include, for example, sterility (nuclear and cytoplasmic), fertility restoration, nutritional enhancements, drought tolerance, nitrogen utilization, industrial enhancements, disease resistance (bacterial, fungal or viral), insect resistance and herbicide resistance. In addition, an introgression site itself, such as an FRT site, Lox site or other site specific integration site, may be inserted by backcrossing and utilized for direct insertion of one or more genes of interest into a specific plant variety. In some embodiments of the disclosure, the number of loci that may be backcrossed into a tomato variety such as, for example, tomato rootstock variety 'RTS-188', is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele involves growing and selfing the first backcross generation to determine which plants carry the recessive alleles. Recessive traits may involve additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, Breeding Field Crops, P. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

Pedigree Breeding

Pedigree breeding starts with the crossing of two genotypes, such as tomato rootstock variety 'RTS-188' and another tomato variety having one or more desirable characteristics that is lacking or which complements tomato rootstock variety 'RTS-188'. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: F1 to F2; F2 to F3; F3 to F4; F4 to F5, etc. After a sufficient amount of inbreeding, successive filial generations will serve to increase seed of the developed variety. Preferably, the developed variety contains homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a tomato variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new tomato varieties.

Therefore, an embodiment of this disclosure is a method of making a backcross conversion of tomato rootstock variety 'RTS-188', involving the steps of crossing a plant of tomato rootstock variety 'RTS-188' with a donor plant having a desired trait, selecting an F1 progeny plant having the desired trait, and backcrossing the selected F1 progeny plant to a plant of tomato rootstock variety 'RTS-188'. This method may further involve the step of obtaining a molecular marker profile of tomato rootstock variety 'RTS-188' and using the molecular marker profile to select for a progeny plant with the desired trait and the molecular marker profile of tomato rootstock variety 'RTS-188'. In one embodiment the desired trait is a mutant gene or transgene present in the donor parent.

Recurrent Selection and Mass Selection

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection may involve growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Thus, another aspect of the disclosure is the use of tomato plants of tomato rootstock variety 'RTS-188' in recurrent selection and/or mass selection breeding schemes and may be used to develop new tomato varieties.

Mutation Breeding

Mutation breeding is another method of introducing new traits into tomato plants of tomato rootstock variety 'RTS-188'. Mutations that occur spontaneously or are artificially induced can be useful sources of variability for a plant breeder. The goal of artificial mutagenesis is to increase the rate of mutation for a desired characteristic. Mutation rates can be increased by many different means including, for example, temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principles of Cultivar Development" Fehr, 1993 Macmillan Publishing Company. In addition, mutations created in other tomato plants may be used to produce a backcross conversion of tomato plants of tomato rootstock variety 'RTS-188' that includes such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing a tomato plant of tomato rootstock variety 'RTS-188'.

Isozyme Electrophoresis and RFLPs have been widely used to determine genetic composition. See, for example, Shoemaker and Olsen, ((1993) Molecular Linkage Map of Soybean (Glycine max L. Men.). p. 6.131-6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994 RFLP Map of Soybean. P. 299-309 In R. L. Phillips and I. K. Vasil (ed.) DNA-based markers in plants. Kluwer Academic Press Dordrecht, the Netherlands.

SSR technology is currently the most efficient and practical marker technology; more marker loci can be routinely used and more alleles per marker locus can be found using SSRs in comparison to RFLPs. For example Diwan and Cregan, described a highly polymorphic microsatellite loci in tomato with as many as 26 alleles. (Diwan, N., and P. B. Cregan 1997 Automated sizing of fluorescent-labeled simple sequence repeat (SSR) markers to assay genetic variation in Soybean Theor. Appl. Genet. 95:220-225.) Single Nucleotide Polymorphisms may also be used to identify the unique genetic composition of the tomato plants described herein and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids may also be used for the development of plants with a homozygous genotype and/or phenotype in the breeding program. For example, a tomato plant for which tomato rootstock variety 'RTS-188' is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetic, 77:889-892, 1989 and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, Am. Nat. 93:381-382; Sharkar and Coe, 1966, Genetics 54:453-464), KEMS (Deimling, Roeber, and Geiger, 1997, Vortr. Pflanzenzuchtg 38:203-224), or KMS and ZMS (Chalyk, Bylich & Chebotar, 1994, MNL 68:47; Chalyk & Chebotar, 2000, Plant Breeding 119:363-364), and indeterminate gametophyte (ig) mutation (Kermicle 1969 Science 166:1422-1424).

Methods for obtaining haploid plants are also disclosed in Kobayashi, M. et al., Journ. Heredity 71(1):9-14, 1980, Pollacsek, M., Agronomie (Paris) 12(3):247-251, 1992; Cho-Un-Haing et al., Journ. of Plant Biol., 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47.

Thus, an embodiment of this disclosure is a process for making a substantially homozygous tomato rootstock variety 'RTS-188' progeny plant by producing or obtaining a seed from the cross of a tomato plant of tomato rootstock variety 'RTS-188' and another tomato plant and applying double haploid methods to the F1 seed or F1 plant or to any successive filial generation. Based on studies in maize and currently being conducted in tomato, such methods would decrease the number of generations required to produce a variety with similar genetics or characteristics to tomato rootstock variety 'RTS-188'. See Bernardo, R. and Kahler, A. L., Theor. Appl. Genet. 102:986-992, 2001. In particular, a process of making seed retaining the molecular marker profile of tomato rootstock variety 'RTS-188' is contemplated, such process involving obtaining or producing F1 seed for which tomato rootstock variety 'RTS-188' is a parent, inducing doubled haploids to create progeny without the occurrence of meiotic segregation, obtaining the molecular marker profile of tomato rootstock variety 'RTS-188', and selecting progeny that retain the molecular marker profile of tomato rootstock variety 'RTS-188'.

Descriptions of other breeding methods that are commonly used for different traits and crops can be found in one of several reference books (e.g., Allard, 1960; Simmonds, 1979; Sneep et al., 1979; Fehr, 1987).

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments of the disclosure and does not pose a limitation on the scope of the disclosure unless otherwise claimed. No language in the specification should be construed as indicating any non-claimed element as essential to the practice of the embodiments of the disclosure.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of tomato rootstock variety 'RTS-188' is maintained by Rootility Ltd., having an address at P.O. Box 7104, Southern Industrial Zone Ashkelon, 7817001, Israel. Access to the deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of tomato rootstock variety 'RTS-188' will be irrevocably removed by affording access to a deposit of at least 2,500 seeds of the variety with the American Type Culture Collection, (ATCC), ATCC Patent Depository, 10801 University Boulevard, Manassas, Va., 20110, USA.

At least 2500 seeds of tomato rootstock variety 'RTS-188' were deposited on Jul. 6, 2017 according to the Budapest Treaty in the American Type Culture Collection (ATCC), ATCC Patent Depository, 10801 University Boulevard, Manassas, Va., 20110, USA. The deposit has been assigned ATCC number PTA-124244. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of 30 years, or 5 years after the most recent request, or for the effective life of the patent, whichever is longer, and will be replaced if a deposit becomes nonviable during that period.

The invention claimed is:

1. Tomato seed designated as 'RTS-188', representative sample of seed having been deposited under ATCC Accession Number PTA-124244.

2. A plant produced by growing the seed of claim 1.

3. A plant part from the plant of claim 2.

4. The plant part of claim 3, wherein said part is selected from the group consisting of rootstocks, leaves, ovules, pollen, fruit, cotyledons, meristems, anthers, roots, root tips, pistils, flowers, stems, calli, stalks, hypocotyls, and pericarps.

5. A rootstock of the plant of claim 2.

6. A tomato plant having all the physiological and morphological characteristics of the tomato plant of claim 2.

7. A plant part from the plant of claim 6.

8. The plant part of claim 7, wherein said part is selected from the group consisting of rootstocks, leaves, ovules, pollen, fruit, cotyledons, meristems, anthers, roots, root tips, pistils, flowers, stems, calli, stalks, hypocotyls, and pericarps.

9. Pollen of the plant of claim 2.

10. An ovule of the plant of claim 2.

11. A tissue culture of the plant of claim 2.

12. A method of making tomato seeds comprising crossing the plant of claim 2 with another tomato plant and harvesting seed therefrom.

13. A tomato plant comprising a rootstock and a scion engrafted onto the rootstock, wherein said rootstock is from tomato rootstock variety 'RTS-188', representative sample of 'RTS-188' tomato seed having been deposited under ATCC Accession Number PTA-124244.

* * * * *